(12) United States Patent  
Yang

(10) Patent No.: US 9,232,970 B2  
(45) Date of Patent: Jan. 12, 2016

(54) FEMORAL FRACTURE FIXATION DEVICE

(71) Applicant: ZIMMER GMBH, Winterthur (CH)

(72) Inventor: Kyu Hyun Yang, Seoul (KR)

(73) Assignee: Zimmer GmbH, Winterthur (CH)

( * ) Notice: Subject to any disclaimer, the term of this patent is extended or adjusted under 35 U.S.C. 154(b) by 0 days.

(21) Appl. No.: 14/157,556

(22) Filed: Jan. 17, 2014

(65) Prior Publication Data

US 2014/0135770 A1     May 15, 2014

Related U.S. Application Data

(62) Division of application No. 13/210,037, filed on Aug. 15, 2011, now Pat. No. 8,652,136.

(51) Int. Cl.
*A61B 17/72* (2006.01)
*A61B 17/74* (2006.01)

(52) U.S. Cl.
CPC ............. *A61B 17/7233* (2013.01); *A61B 17/72* (2013.01); *A61B 17/744* (2013.01)

(58) Field of Classification Search
USPC ..................................... 606/62–68
See application file for complete search history.

(56) References Cited

U.S. PATENT DOCUMENTS

| | | | |
|---|---|---|---|
| 2,381,050 A * | 8/1945 | Hardinge | 606/65 |
| 2,397,545 A * | 4/1946 | Hardinge | 606/65 |
| 2,685,877 A * | 8/1954 | Dobelle | 623/23.11 |
| 3,489,143 A | 1/1970 | Halloran | |
| 4,129,903 A | 12/1978 | Huggler | |
| 4,236,512 A * | 12/1980 | Aginsky | 606/68 |
| 4,791,918 A | 12/1988 | Von Hasselbach | |
| 5,167,666 A | 12/1992 | Mattheck et al. | |
| 6,447,513 B1 * | 9/2002 | Griggs | 606/62 |
| 8,449,583 B2 * | 5/2013 | Krebs et al. | 606/300 |
| 8,652,136 B2 | 2/2014 | Yang et al. | |
| 2003/0073999 A1 | 4/2003 | Putnam | |
| 2005/0182405 A1 * | 8/2005 | Orbay et al. | 606/69 |
| 2006/0155281 A1 * | 7/2006 | Kaup et al. | 606/65 |
| 2007/0123873 A1 | 5/2007 | Czartoski et al. | |
| 2007/0123874 A1 | 5/2007 | Czartoski et al. | |
| 2008/0294164 A1 | 11/2008 | Frank et al. | |
| 2010/0198276 A1 * | 8/2010 | Krebs et al. | 606/86 R |
| 2011/0137356 A1 | 6/2011 | Kollmer | |
| 2013/0046307 A1 | 2/2013 | Yang | |

FOREIGN PATENT DOCUMENTS

| | | |
|---|---|---|
| WO | WO-2007054591 A1 | 5/2007 |
| WO | WO-2013024356 A2 | 2/2013 |

OTHER PUBLICATIONS

"U.S. Appl. No. 13/210,037, Corrected Notice of Allowance mailed Oct. 28, 2013", 7 pgs.
"U.S. Appl. No. 13/210,037, Examiner Interview Summary mailed Jun. 3, 2013", 3 pgs.

(Continued)

*Primary Examiner* — Jan Christopher Merene

(74) *Attorney, Agent, or Firm* — Schwegman Lundberg & Woessner, P.A.

(57) ABSTRACT

A femur fixation device including an elongated nail configured for insertion into the medullary canal of the femur and a buttress element extending from the elongated nail. The buttress element is configured to reinforce the lesser trochanter region of the femur and assist in stabilizing the head portion of the femur.

20 Claims, 10 Drawing Sheets

(56) References Cited

OTHER PUBLICATIONS

"U.S. Appl. No. 13/210,037, Non Final Office Action mailed May 13, 2013", 11 pgs.

"U.S. Appl. No. 13/210,037, Notice of Allowance mailed Sep. 26, 2013", 9 pgs.

"U.S. Appl. No. 13/210,037, Response filed Aug. 29, 2013 to Non Final Office Action mailed May 13, 2013", 12 pgs.

"U.S. Appl. No. 13/210,037, Restriction Requirement mailed Mar. 27, 2013", 6 pgs.

"International Application Serial No. PCT/IB2012/001997, International Search Report mailed Feb. 19, 2013", 4 pgs.

"International Application Serial No. PCT/IB2012/001997, Written Opinion mailed Feb. 19, 2013", 7 pgs.

* cited by examiner

FEMORAL FRACTURE FIXATION DEVICE

CLAIM OF PRIORITY

This application is a divisional of U.S. patent application Ser. No. 13/210,037, filed on Aug. 15, 2011, and issued on Feb. 18, 2014 as U.S. Pat. No. 8,652,136, the benefit of priority of which is claimed hereby, and is incorporated by reference herein in its entirety.

FIELD OF THE DISCLOSURE

The present disclosure generally relates to bone fracture fixation devices and, more particularly, to bone fracture fixation devices that include a bone reinforcement element for reinforcing a region of damaged or deformed bone. Even more particularly, the present disclosure relates to an intramedullary nail including a lesser trochanter reinforcement member for reinforcing the lesser trochanter region of a damaged femur.

BACKGROUND

Fractures at or near the proximal end portion of the femur may occur in any area of the proximal end and oftentimes occur in multiple locations. FIG. 1 illustrates a femur 10 including a fracture 12 in the proximal end portion 14 of the femur. Femur 10 includes a neck portion 16, a trochanteric portion 17, a head portion 18 and a body 20. As shown in FIG. 1, fracture 12 is located in neck portion 16 or trochanteric portion 17, between head portion 18 and the body 20. When such a fracture occurs, the lower or lesser trochanter region 22 may become comminuted into fragmented pieces 24 that are separated from proximal end portion 14 of femur 10.

One device commonly employed to stabilize and fixate a fractured proximal end of the femur with a comminuted lesser trochanter is an intramedullary nail. FIG. 2 illustrates an intramedullary nail 26 that has been inserted and fixed within femur 10 having a proximal end fracture 12. Typically, during a minimally invasive procedure, intramedullary nail 26 is inserted through proximal end 14 of femur 10 and into the medullary canal of femur 10. One or more cortical screws 30 may then be inserted through the cortical bone of one side of femur body 20, through a bore 32 extending through intramedullary nail 26 and into the cortical bone of the other side of femur body 20.

A lag screw 34 is inserted through the cortical bone and a bore 36 in the proximal end portion 38 of the intramedullary nail 26. Lag screw 34 includes a distal end portion 40 that is inserted into head portion 18 of femur 10. Distal end portion 40 of the lag screw 34 engages trabecular or cancellous bone within head portion 18 of femur 10. Distal end portion 40 of lag screw 34 may include an engaging member or members, such as threads, that engage the cancellous bone of head portion 18. After lag screw 34 has engaged head portion 18, the head portion is pulled by lag screw 34 toward neck portion 16 and body 20 of femur 10 to rejoin head portion 18 with femur 10 at fracture 12 as shown in FIG. 3.

When a patient, having an intramedullary nail implanted within a femur 10, places pressure on the affected leg, the acetabulum of the pelvic bone places outward and downward pressure on head portion 18 of the femur. Because the lesser trochanter has been comminuted and separated from the bone, the lesser trochanter region 24 is essentially void and does not provide much, if any, support to head portion 18. As illustrated in FIG. 3, the downward pressure on head portion 18 from the acetabulum may cause head portion 18 to rotate in a downward direction, as indicated by arrow A. The acetabulum may also place outward pressure on head portion 18 that may cause head portion 18 and lag screw 34 to move into an anatomically incorrect position, e.g., too far towards neck 16 and body 20 of femur 10.

Downward rotation of head portion 18 may cause the cancellous bone in the region designated as 42 of head portion 18 to press against distal end portion 40 of lag screw 34. The pressure of the cancellous bone against distal end portion 40 of lag screw 34 may cause strain and further injury to the bone in region 42, which may cause further bone fracture or injury to head portion 18. Furthermore, downward rotation of head portion 18 may cause the lower region 46 of head portion 18 to be moved toward body 20, past its anatomically correct position.

Typically, lag screw 34 is designed to allow for some degree of movement of head portion 18 relative to trochanteric portion 17 and body 20. However, the outward pressure placed on head portion 18 may cause lag screw 34 and head portion 18 to move outward, as indicated by arrow B, and in some instances head portion 18 may be pushed into trochanteric portion 17 and body 20 beyond its natural anatomical proposition. This may result in the head portion healing in an incorrect or unnatural anatomical position, which may cause lingering or prolonged pain to the patient after the fracture has healed.

SUMMARY

In one aspect, the present disclosure relates to a femur fixation device including an elongated nail configured for insertion into the medullary canal of the femur and a buttress element extending from the elongated nail. The buttress element is configured to apply a force to bone tissue in or adjacent to the lesser trochanter region of the femur. In one embodiment, the buttress element assists in stabilizing or fixing the head portion of the femur. The buttress element also may prevent or limit downward rotation or outward movement of the femur head.

In another aspect, the present disclosure relates to a femur fixation device including an elongated nail adapted for insertion into the medullary canal of the femur and a buttress element associated with the nail. The buttress element is configured for reinforcing the lesser trochanter region of the femur.

In yet another aspect, the present disclosure is related to a method of treating a femur including inserting an elongated nail into an intramedullary canal of the femur and reinforcing a lesser trochanter region of the femur with a buttress element that extends from the elongated nail. The buttress element may assist in stabilizing the head portion of the femur. The buttress element also may limit or prevent outward or downward movement of the head portion of the femur.

BRIEF DESCRIPTION OF THE FIGURES

In the course of this description, reference will be made to the accompanying drawing(s), wherein.

DETAILED DESCRIPTION

As required, detailed embodiments of the present invention are disclosed herein; however, it will be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 4:
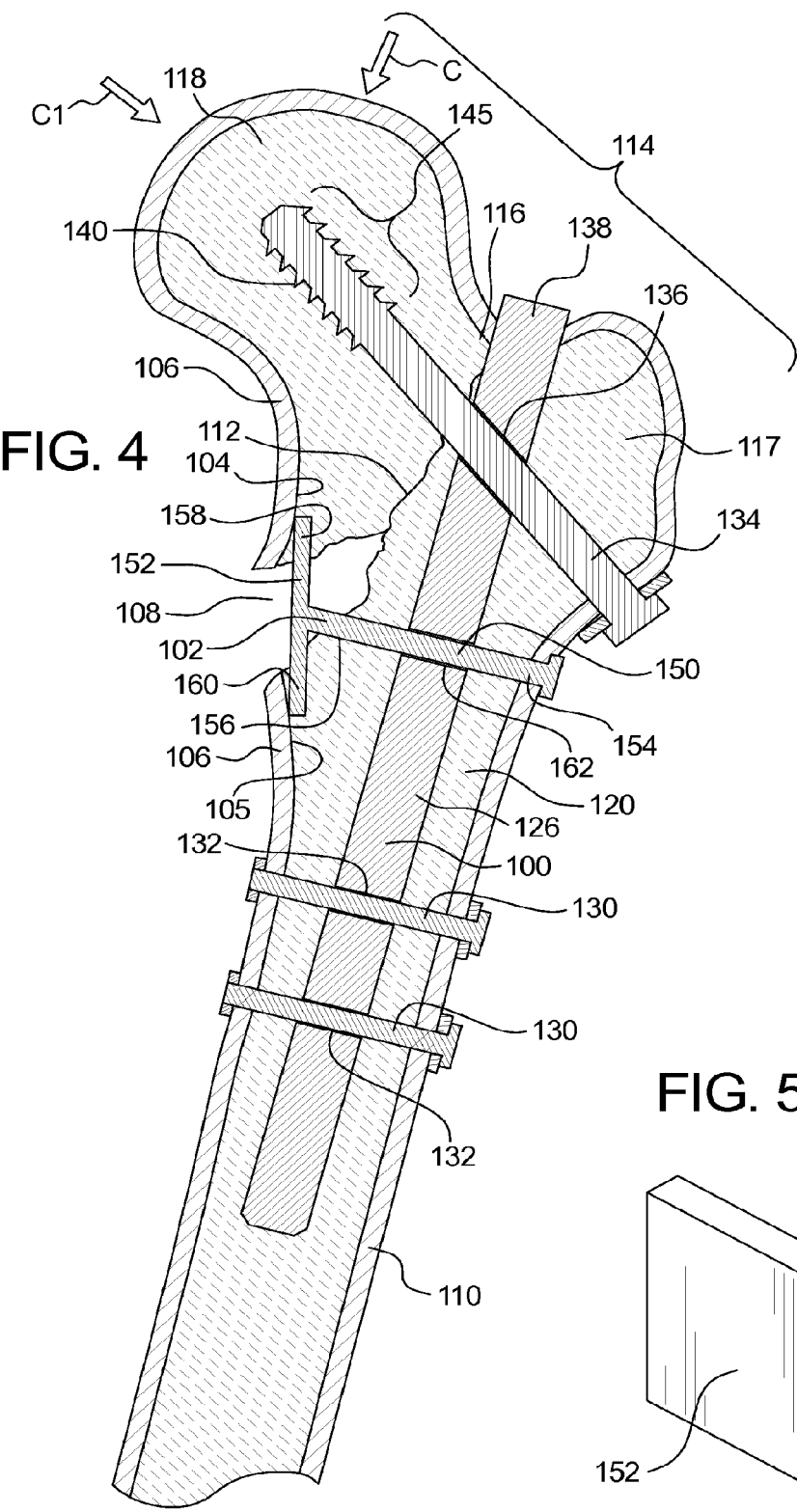
FIG. 4 is a cross-sectional view of a fractured femur shown with one embodiment of a fracture fixation device of the present disclosure implanted therein.

FIG. 4 illustrates one embodiment of a fracture fixation device 100 of the present disclosure shown within a femur 110 having a proximal end fracture 112 wherein the lesser trochanter has been comminuted and separated from the bone. Device 100 is implanted into femur 110 to stabilize and heal the fractured segments of the bone. As will be explained in more detail below, device 100 includes an intramedullary nail 126 and a buttress element 102 associated with intramedullary nail 126. Buttress element 102 contacts the inner wall 104 of the cortical bone 106 or other tissue above damaged lesser trochanter region 108. In some embodiments, buttress element 102 also contacts inner wall 103 of the cortical bone 105 or other tissue below damaged lesser trochanter region 108 to assist in stabilizing head portion 118 of femur 110 relative to neck 116 and body 120 of the femur 110. In particular, buttress element 102, in this embodiment, spans the region 108 of the comminuted or otherwise damage lesser trochanter to stabilize head portion 118. Buttress element 102, may among other things, reduce or prevent the amount of rotation of head portion 118 and/or the amount of outward sliding or movement of head portion 118 when pressure is applied to the head portion in the direction of arrow C and/or C1.

Figure 1:
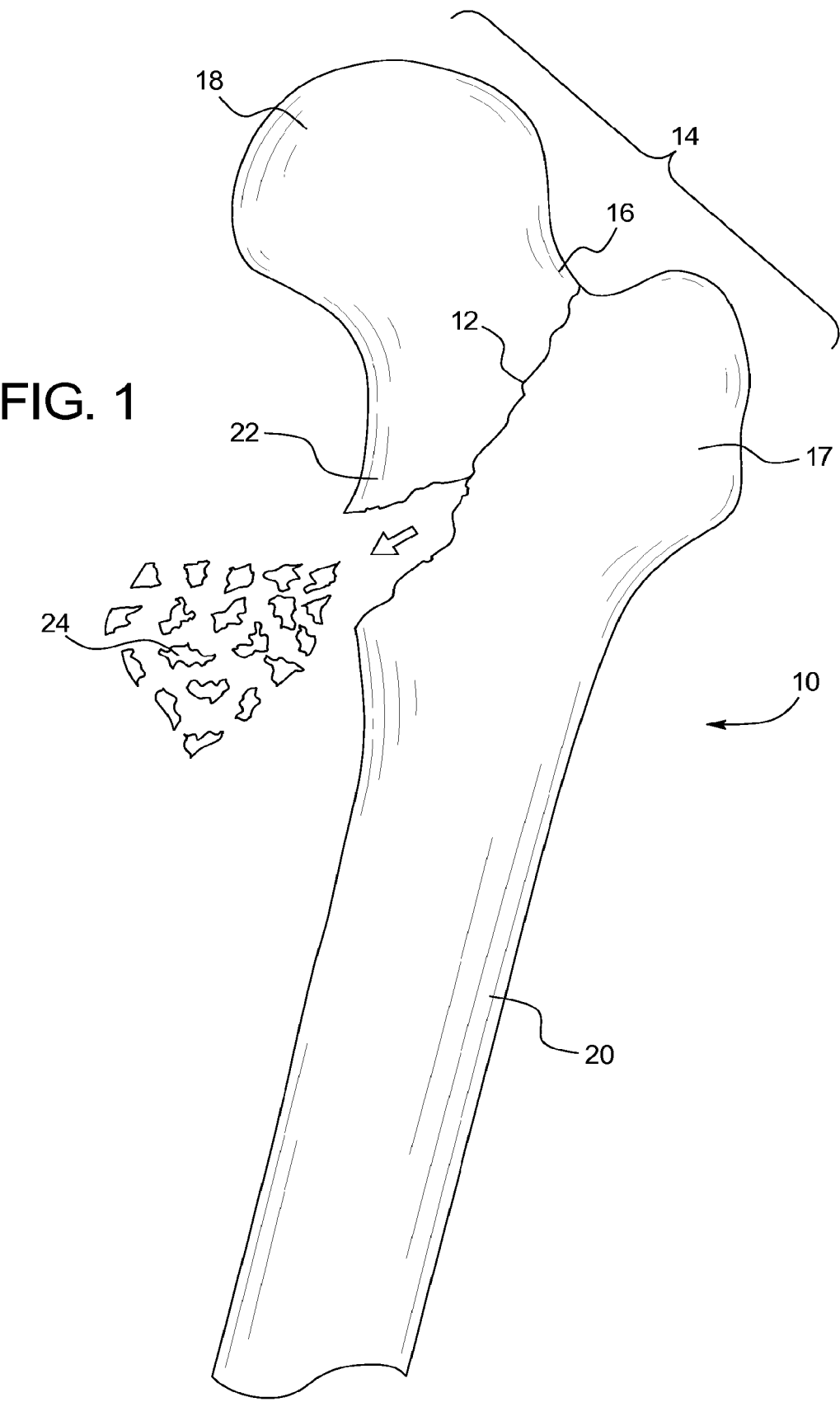
FIG. 1 is a frontal view of a femur having a proximal end fracture wherein the lesser trochanter has been comminuted.
Figure 2:
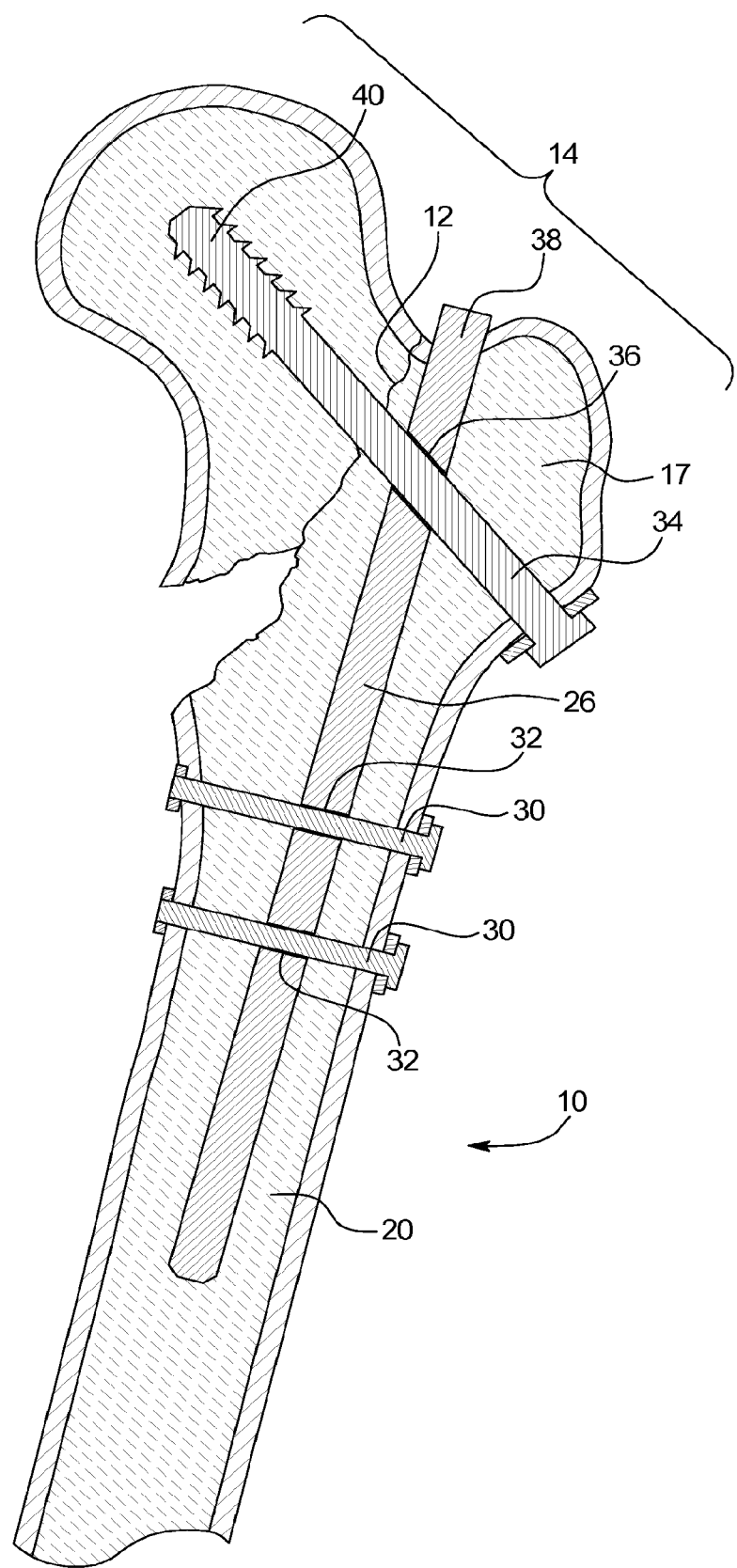
FIG. 2 is a cross-sectional view of a fractured femur shown with a prior art fixation device implanted in the femur for treatment of the fracture.

Intramedullary nail 126 may be of any design known in the art and may include for example, features such as bends, angles, spirals, flutes, etc. Intramedullary nail 126 is inserted through the proximal end 114 of femur 110 and into the intramedullary cavity of femur body 120. As shown in FIG. 4, head portion 118 of femur 110 is separated from body 120 by fracture 112. Fixation device 100 also may include a one or more lag screws 134 that are employed to connect head portion 118 to body 120 of femur 110. In the illustrated embodiment, fixation 100 device includes one lag screw 134 which is inserted (1) through the cortical bone of femur 110, (2) through a bore 136 in the proximal end portion 138 of intramedullary nail 126, and (3) into head portion 118. Lag screw 134 engages head portion 118 of femur 110 to fix and stabilize head portion 118 relative to femur body 120. Similar to lag screw 34 of FIGS. 2 and 3, lag screw 134 includes a threaded distal end portion 140 the contacts and engages the inner cancellous bone of head portion 118.

Fixation device 100 also may include one or more fasteners, such as locking screws 130, which secure intramedullary nail 126 within the femur 110. Locking screws 130 are inserted (1) through one side of femur body 120, (2) through bores 132 of intramedullary nail 126, and (3) into the other side of the bone of femur body 120.

As discussed above, fixation device 100 includes a buttress element 102 that extents from intramedullary nail 126 and contacts inner wall 104 of cortical bone 106 or adjacent tissue to apply a force to cortical bone 106. Buttress element 102 may include a supporting member 150 and a reinforcement member 152. In the illustrated embodiment, supporting member 150 is elongated member, such as a post, rod, stem or shaft, which includes a proximal end portion 154 and a distal end portion 156. Reinforcement member 152 is located at or adjoins distal end portion 156 of support member 150. As illustrated in FIG. 4, reinforcement member 152 includes an upper portion 158 that contacts the portion of cortical bone 106 above the damaged lesser trochanter region 108, and a bottom portion 160 the contacts the cortical bone 105 below the damaged lesser trochanter region 108. In some embodiments, the reinforcement member 152 may only contact the cortical bone 106 above damaged less trochanter region 108.

Figure 5:
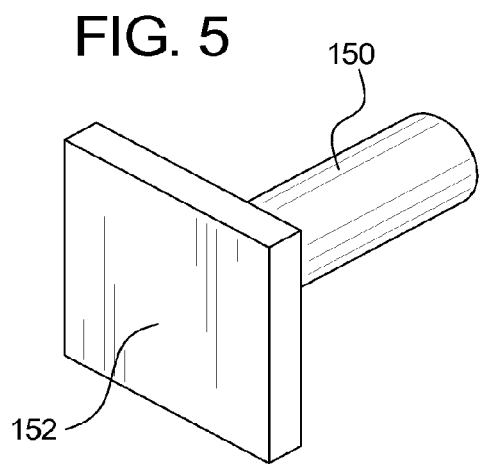
FIG. 5 is a perspective view of one embodiment of a buttress element of the present disclosure.

FIG. 5 illustrates one embodiment of a buttress element 102 wherein support member 150 is an elongated rod and reinforcement member 152 is a square or rectangular plate-like member. In this embodiment, reinforcement element 152 extends in a direction transverse to the longitudinal axis of support member 150. Reinforcement member 152 also may be other configurations, such as circular, oval, regular or irregular polygonal shapes of various sizes.

Referring back to FIG. 4, in this embodiment, support member 150 of buttress element 102 extends through the cortical bone of femur body 120 and through a bore 162 in intramedullary nail 126. Reinforcement member 152 contacts the inner wall 104 of the cortical bone 106 in the lesser trochanter region to assist in stabilizing head portion 118. Proximal end portion 154 of support member 150 may be anchored to the cortical bone of femur body 120 to secure buttress element 102 in the desire position. Buttress element 102 provides a force which reduces, limits or prevents downward rotation and outward movement of head portion 118.

For example, as described above with respect to FIG. 3, when downward pressure is placed on head portion 18, the head portion may rotate in a downward direction resulting in (1) pressure of the in cortical bone in region 42 against distal end portion 40 of lag screw 34 and (2) separation of head portion 18 from trochanteric portion 17 and body 20 in the upper fracture site 44. Pressure of the bone against lag screw 34 and sliding of head portion 18 and neck 16 into the fracture site may result in patient pain and discomfort and unnatural healing of the bone.

With reference to FIG. 4 and fixation device 100 of the present disclosure, when downward pressure is placed on head portion 118 of femur 110 as indicated by arrow C, the upper portion 158 of reinforcement member 152 in contact with or applying a force to a portion of the cortical bone 106 above the damaged lesser trochanter region 108 buttresses or reinforces cortical bone 106. The reinforcement provided by the buttress element 102 stabilizes head portion 118 and reduces, limits or prevents head portion 118 from rotating downward. Preventing or limiting the downward rotational movement head portion 118 reduces, prevents or limits the pressure of the cancellous bone in region 145 against distal end portion 140 of lag screw 134 and prevents head portion 118 from pulling away from neck 116 and body 120 in the upper area of the facture 112.

Figure 3:
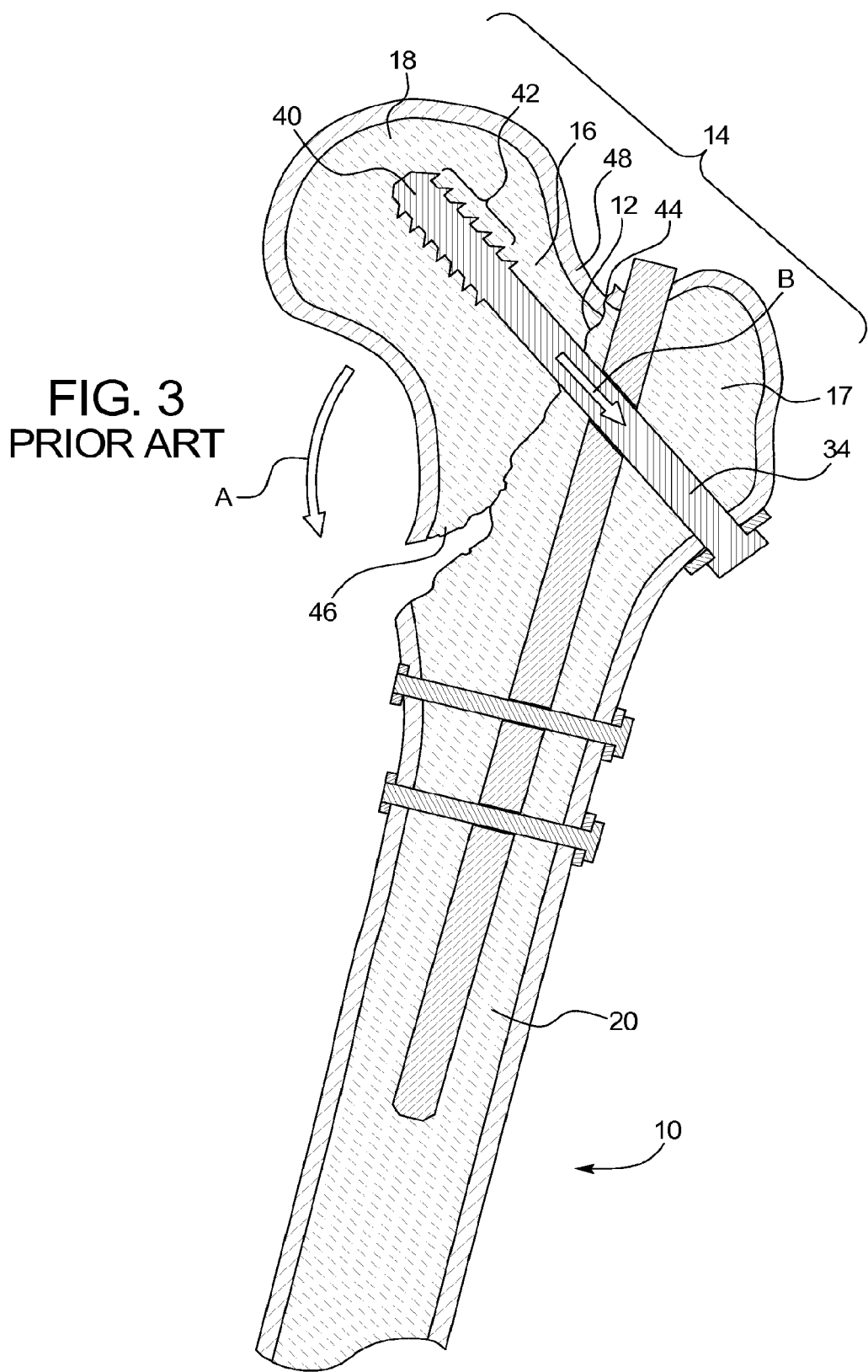
FIG. 3 is a cross-sectional view of the fractured femur and prior art treatment device of FIG. 2 which shows the movement of the femur's head portion relative to the femur's trochanter and body in response to pressure placed on the head portion.

Also as described above with respect to FIG. 3, lag screw 34 is designed to allow some inward and outward movement of head portion 18 relative to trochanteric portion 17 and body portion 20. However, if too much outward pressure is placed on head portion 18 or lag screw 134 allows too much outward movement, head portion 18 may over slide or be pressed too far into trochanteric portion 17 and body portion 20. This may result in the head portion healing in an incorrect anatomical position, as shown in FIG. 3.

With fixation device 100 described herein and as shown in FIG. 4, when outward pressure is placed on head portion 118, the upper portion 158 of reinforcement member 152 in contact with the inner wall 104 of the cortical bone 106 above the damaged lesser trochanter region 108 buttresses, reinforces or applies a force to the cortical bone 106. The reinforcement provided by the buttress element 152 stabilizes head portion 118 by acting as a stop that prevents outward movement of head portion 118 beyond a desired point. Preventing head portion 118 from moving outward beyond a desired point retains head portion 118 in a substantially anatomically correct position and reduces the risk of head portion 118 from healing in an incorrect anatomical position.

Figure 6A:
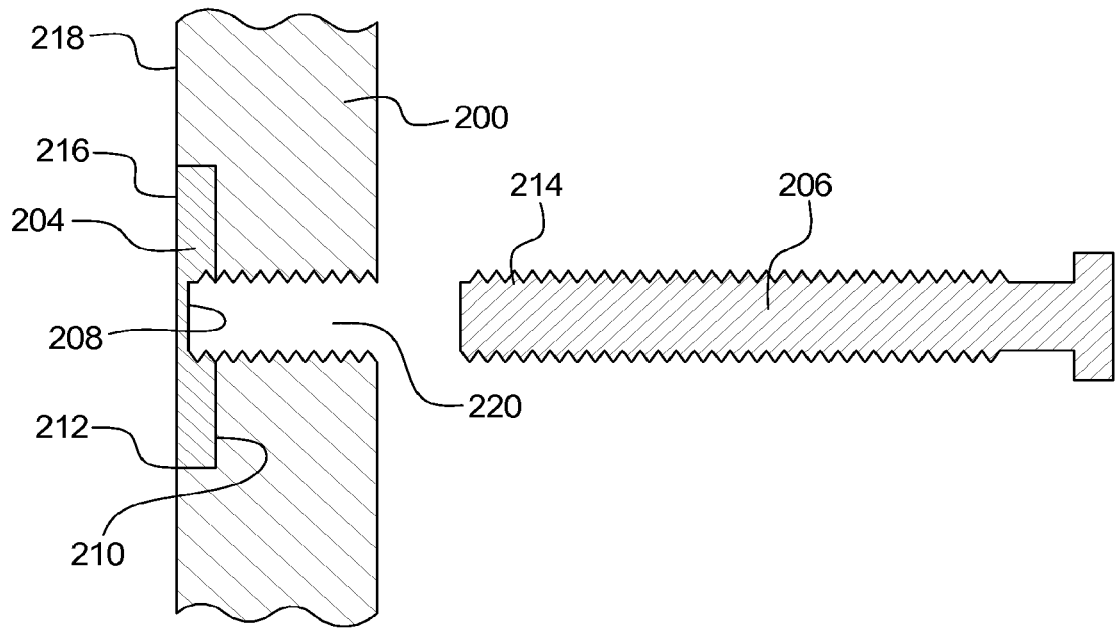
FIG. 6A is a cross-sectional view of one embodiment of a buttress element and a section of an intramedullary nail of the present disclosure with the buttress element in a pre-deployed position.

FIGS. 6A-10B illustrate some exemplary embodiments of the buttress element of the present disclosure. FIGS. 6A and 6B are cross-sectional views of a section of an intramedullary nail 200 and a buttress element 202 (as shown in FIG. 6B). Buttress element 202 includes a reinforcement member 204 and a support member 206. In this embodiment, the reinforcement member 204 and support member 206 are provided as two separate pieces which join together to form buttress element 202. Reinforcement member 204 may be a plate-like element which includes a threaded recess 208 within the inner surface 210 of reinforcement member 204. The support member 206 is a threaded support member and the threaded distal end portion 214 of support member is configured to engage thread recess 208 of reinforcement member 204 to attach support member 206 with reinforcement member 204.

Referring to FIG. 6A, in an initial or pre-deployed position, reinforcement member 204 is positioned within a recess 212 in the wall of the intramedullary nail 200. In the illustrated embodiment, the outer surface 216 of reinforcement member 204 is substantially flush with the outer surface 218 of intramedullary nail 200. In other embodiments, the front surface 216 of reinforcement member 204 may extend beyond or be recessed within outer surface 218 of intramedullary nail 200. Furthermore, reinforcement member 204 may be held within recess 212 by a friction fit or by an adhesive. When in this initial position, intramedullary nail 200, with reinforcement member 204 located in recess 212 may be inserted into the intramedullary cavity of the bone.

Figure 6B:
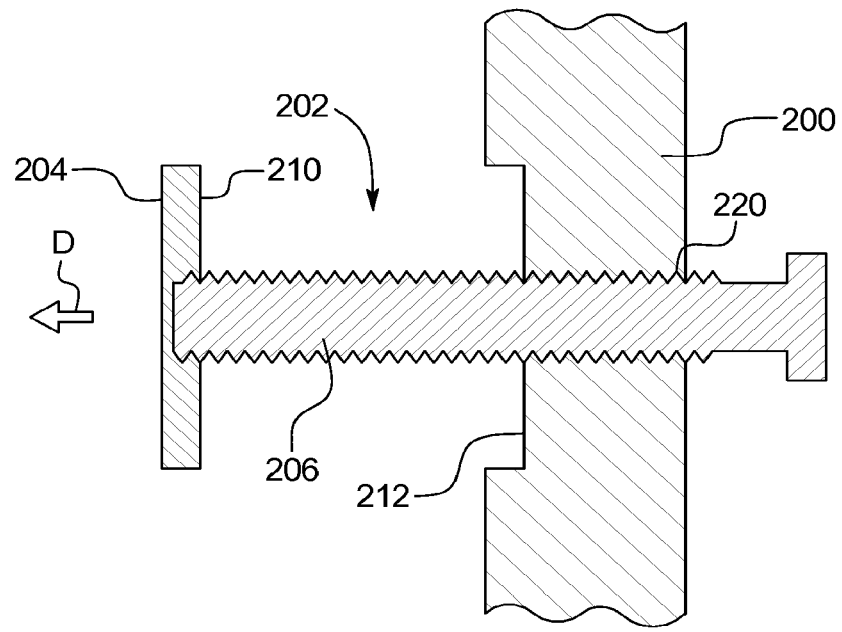
FIG. 6B is a cross-sectional view of the buttress element and intramedullary nail of FIG. 6A with the buttress element shown in a deployed position.

After intramedullary nail 200 is implanted in the desired position, support member 206, is inserted through the cortical bone (not shown) and into a threaded bore 220 passing through intramedullary nail 200. As shown in FIG. 6B, threaded support member 206 mates with the threads of bore 220 and support member 206 is rotated to advance support member 206 through bore 220. As support member 206 is advanced, distal end portion 214 of the support member 206 engages and mates with threaded recess 208 of reinforcement member 204 to adjoin reinforcement member 204 and support member 206. With reinforcement member 204 adjoined to support member 206, support member 206 is further rotated to advance support member 206 and to move reinforcement member 204 from recess 212 and in the direction of arrow D. Support member 206 is rotated until reinforcement member 204 comes into contact with cortical bone 106 of the lesser trochanter region 108, as shown in FIG. 4. In this embodiment the connection between recess 208 of reinforcement member 204 and distal end portion 214 of support member 206 may be such that reinforcement member 204 is connected to support member 206 but does not rotate as supporter member 206 rotates.

Figure 7A:
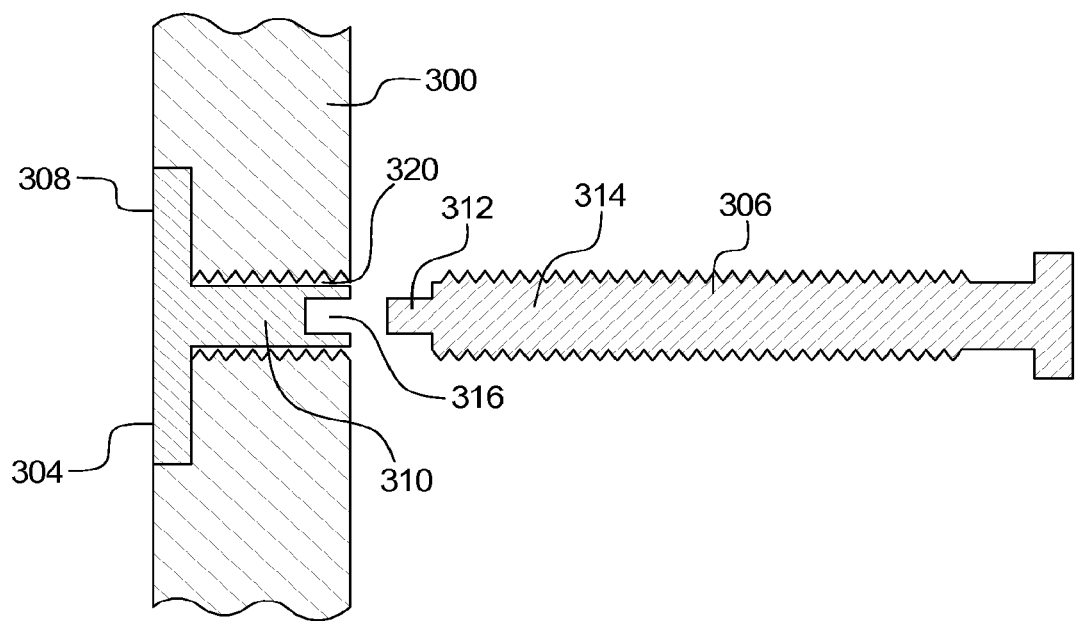
FIG. 7A is a cross-sectional view of another embodiment of a buttress element and a section of an intramedullary nail of the present disclosure with the buttress element shown in a pre-deployed position.
Figure 7B:
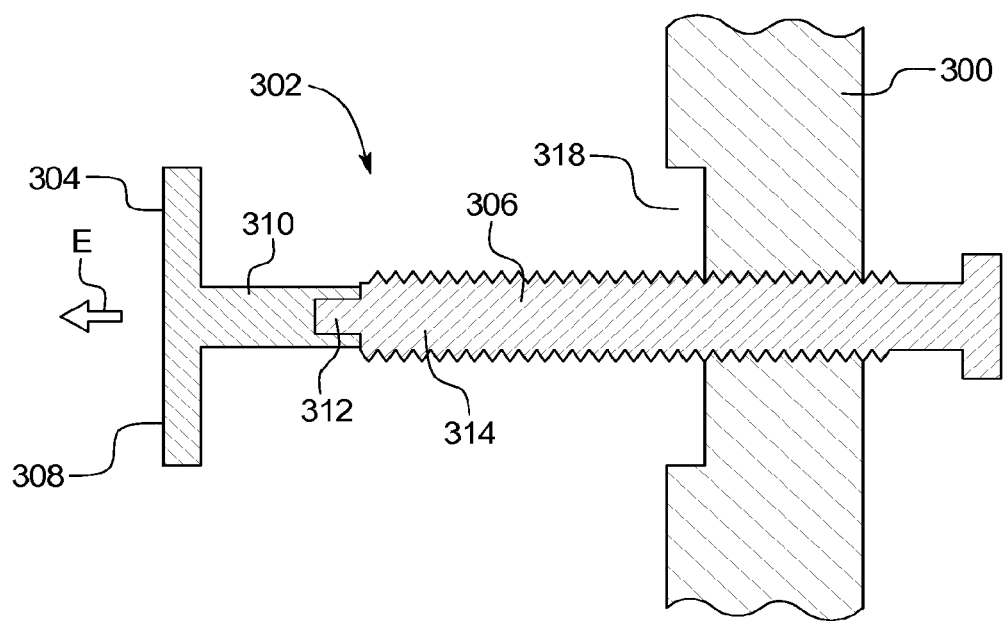
FIG. 7B is a cross-sectional view of the buttress element and intramedullary nail of FIG. 7A with the buttress element shown in a deployed position.

FIGS. 7A and 7B illustrate another embodiment of a buttress element 302 and a section of an intramedullary nail 300. Buttress element 302 (as shown in FIG. 7B) includes a reinforcement member 304 and a support member 306. The reinforcement member 304 includes a plate-like element 308 and a stem 310 extending therefrom. Support member 306 is threaded and includes a joining member, which may be a post 312, located at the distal end portion 314 of support member 306. The post 312 is received into a joining receptacle 316 in stem 310 of reinforcement member 304 to join reinforcement member 304 to support member 306.

Intramedullary nail 300 includes a recess 318 in the wall of the nail and a threaded bore 320 aligned with recess 318. Plate-like portion 308 of reinforcement member 304 is nested within recess 318 and stem 310 of reinforcement member 304 is located within threaded bore 320. After intramedullary nail 300 with reinforcement member 304 has been inserted into the medullary canal of the femur and placed in the desired position, support member 306 is inserted through the cortical bone (not shown) of the femur and into bore 320 of intramedullary nail 300. The post 312 of support member 306 enters the receptacle 316 of the stem 310 of reinforcement member 304 to join support member 306 to reinforcement member 304. Additionally, the threads of support member 306 mate with the threads of bore 320 such that rotation of support member 306 within bore 320 advances support member 306 through the bore. Support member 306 is rotated to push reinforcement member 304 out of recess 318 in the direction of arrow E. Support member 306 is rotated to move reinforcement member 304 into contact with the cortical bone 106 of the lesser trochanter region 108, as shown in FIG. 4.

Figure 8A:
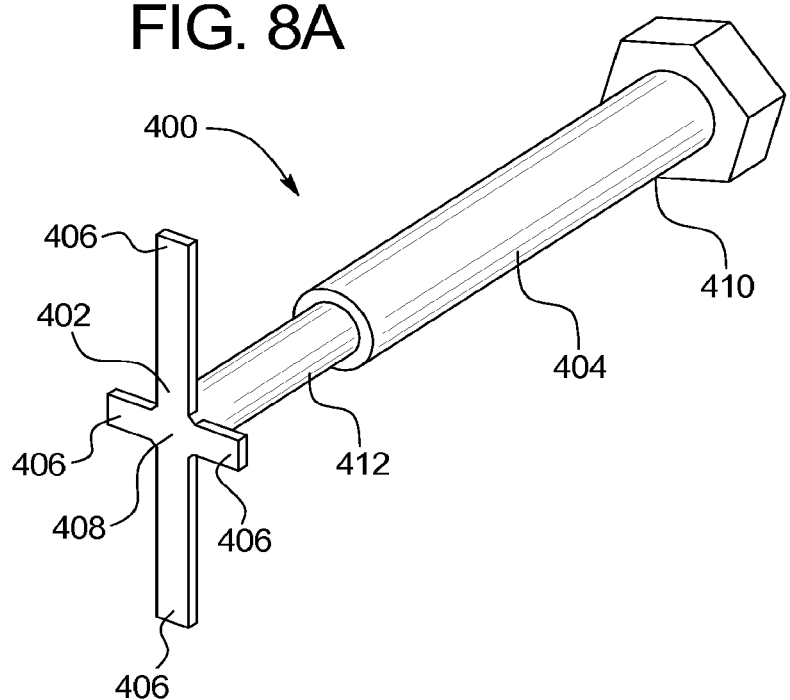
FIG. 8A is a perspective view of a further embodiment of a buttress element of the present disclosure shown in a deployed position.
Figure 8B:
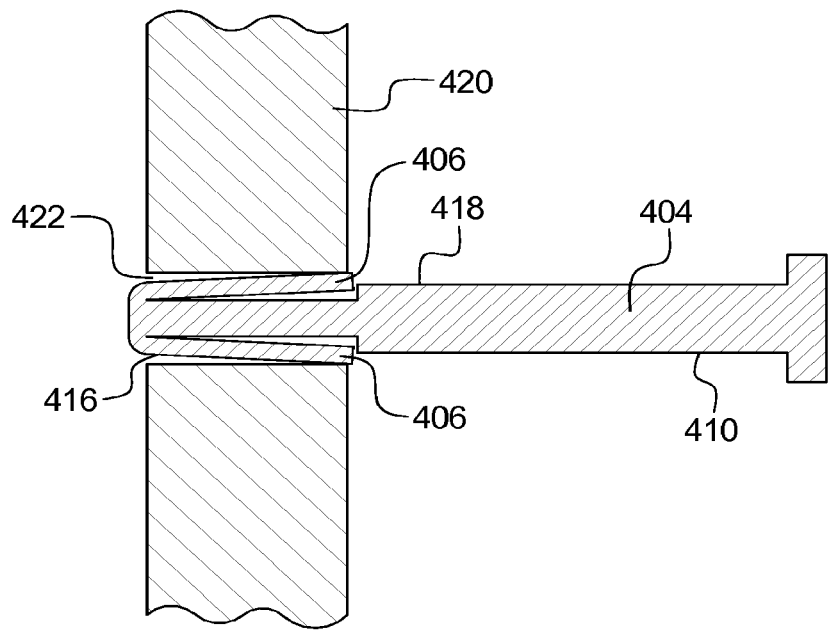
FIG. 8B is a cross-sectional view of the buttress element of FIG. 8A and a section of an intramedullary nail wherein the buttress element has been deformed for insertion through the intramedullary nail.

FIGS. 8A and 8B illustrate another embodiment of a buttress element 400. Buttress element 400 includes a reinforcement member 402 and a support member 404. The reinforcement member 402 may include at least one reinforcement projection or arm 406 that extend(s) or splay(s) radially outward from the center 408 of reinforcement member 402 and is configured to contact and reinforce the cortical bone in lesser trochanter region. In one embodiment, the reinforcement member 402 includes a plurality of reinforcement arms 406. In the illustrated embodiment, the reinforcement member 402 includes fours arms 406 in a generally cruciform configuration.

In one embodiment, reinforcement arms 406 are made from a material that may be deformed from its original configuration for insertion into the femur. Once inserted into the femur, the material is such that the reinforcement arms 406 return to their original configuration. For example, reinforcement member 402 may be made of a shape member alloy or a shape member of polymer. In other embodiments reinforcement arms 406 may include a mechanical mechanism, such as hinges and/or biasing mechanisms, that allows arms 406 to be moved between a splayed and non-splayed configurations.

Support member 404 is rod-shaped and includes a proximal end portion 410 and a reduced diameter distal end portion 412. Referring to FIG. 8B, the reinforcement arms 406 may be deformed into a non-splayed configured by bending arms 406 backwards. In this configuration, arms 406 are bent toward the reduced diameter portion 412 of the support member 404. The reduced diameter portion 412 allows the arms to be bent backwards such that surface 416 of the arms 406 when folded have an outer diameter substantially equal to the outside diameter of proximal end portion 410 of support member 404.

Referring to FIG. 8B, after intramedullary nail 420 has been inserted into and positioned within the intramedullary canal of femur (not shown), buttress element 400 with reinforcement arms 406 in the non-splayed configuration is inserted through the cortical bone (not shown) of the femur and through a bore 422 that extends through intramedullary nail 420. Once the reinforcement arms 406 have cleared or passed through the bore 422, arms 406 are returned to the splayed configuration illustrated in FIG. 8A. When the arms 406 are made from a shape memory material, they may self return to the splayed configuration. One the other hand, if the movement of arms 406 is controlled by a mechanical mechanism, the mechanism may be activated to splay the arms. Support member 404 is advanced through bore 422 until reinforcement arms 406 are in contact with the cortical bone 106 of the lesser trochanter region 108 as shown in FIG. 4.

Figure 9A:
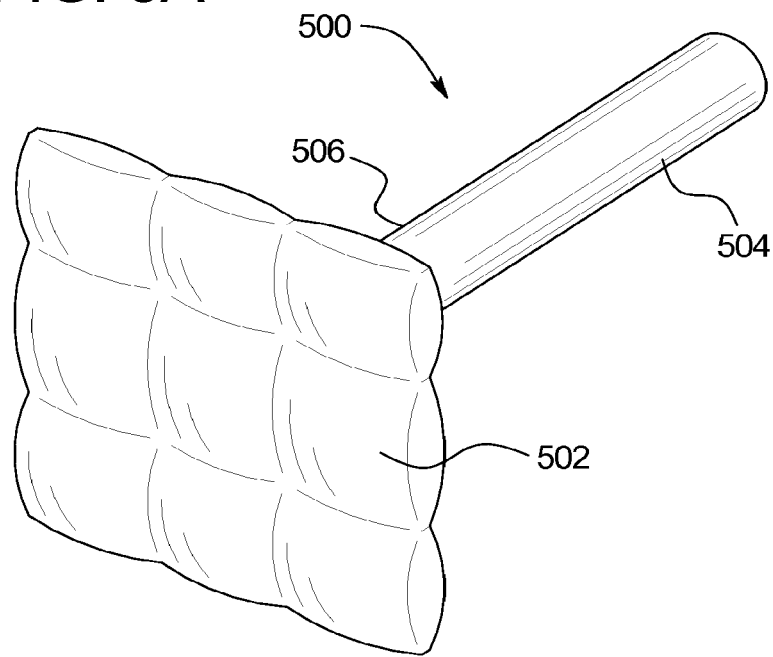
FIG. 9A is a perspective view of another embodiment of a buttress element of the present disclosure shown in a deployed position.
Figure 9B:
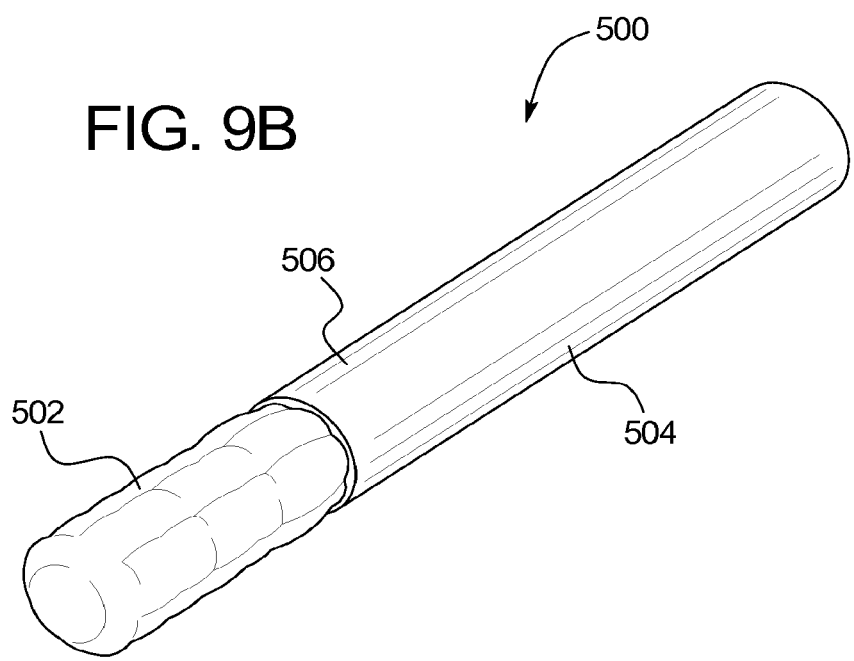
FIG. 9B is a perspective view of the buttress element of FIG. 9A shown in a pre-deployed position.

FIGS. 9A and 9B illustrate yet another embodiment of a buttress element 500 of the present disclosure. Similar to the previous embodiments, the buttress element 500 includes a reinforcement member 502 and a support member 504. In this embodiment, the reinforcement member 502 is an inflatable element, for example a balloon or bag, which may be filled with a hardenable or curable material. FIG. 9A shows the inflatable reinforcement member 502 in the inflatable configuration and FIG. 9B shows the inflatable reinforcement member 502 in the deflated configuration. The inflatable reinforcement member 502 may be any variety of shapes and sizes, for example, circular, square, elongated, etc. Additionally, the reinforcement member 502 may be made of a suitable polymer material, such as polyolefins, polyethylene, polycarbonate, polyethylene terephthalate, ether-ketone polymers and copolymers thereof.

The inflatable reinforcement member 502 is located at the distal end portion 506 of the support member 504. The support member may include a passageway (not shown) for delivering flowable, curable material into the inflatable reinforcement member 502. Such material may be any suitable curable material that when cured is sufficiently strong to reinforce the cortical bone of the lesser trochanter region. In one example, the hardenable, flowable material may be polymethyl methacrylate.

During use, an intramedullary nail is inserted into the medullary canal of a femur. After the nail is in position, the buttress element 500 with the reinforcement member 502 in the deflated condition is inserted through the cortical bone and through a bore in the intramedullary nail. After the deflated reinforcement member 502 has cleared or passed through the bore, flowable, curable material is injected through the passageway in the support member 504 and into the inflatable reinforcement member 502. The flowable material is injected at a pressure sufficient to inflate the reinforcement member 502. The support member 504 and the inflated reinforcement member 502 are advanced through the bore in the intramedullary nail until the reinforcement member is located adjacent to and preferably in contact with the cortical bone 106 of the lesser trochanter region 108, as illustrated in FIG. 4.

Figure 10A:
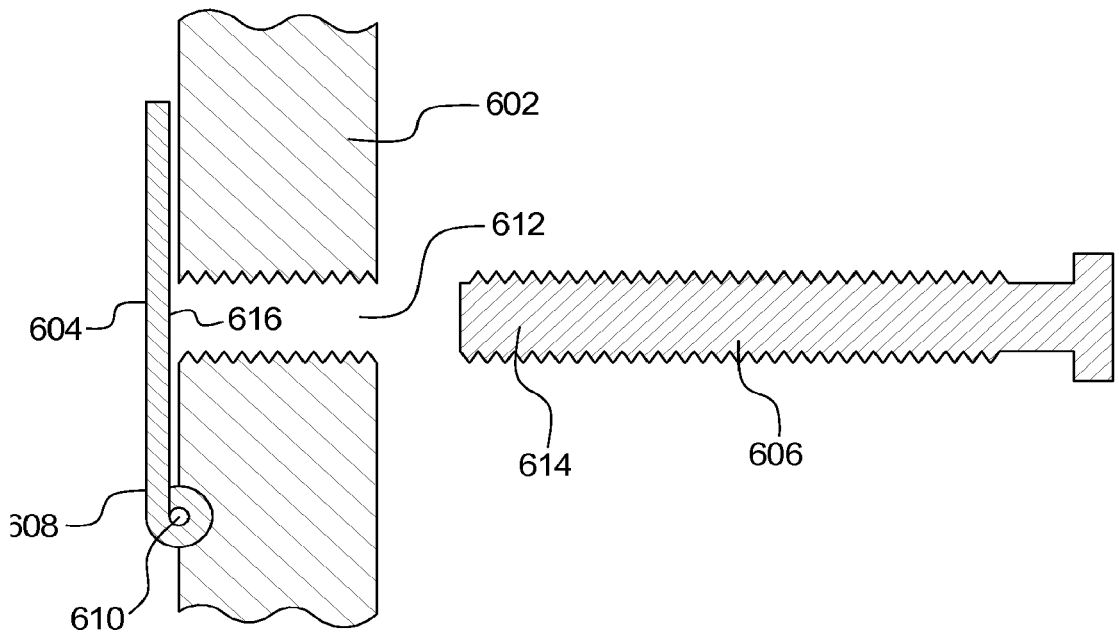
FIG. 10A is a cross-sectional view of another embodiment of a buttress element and a section of an intramedullary nail of the present disclosure shown in a pre-deployed position.
Figure 10B:
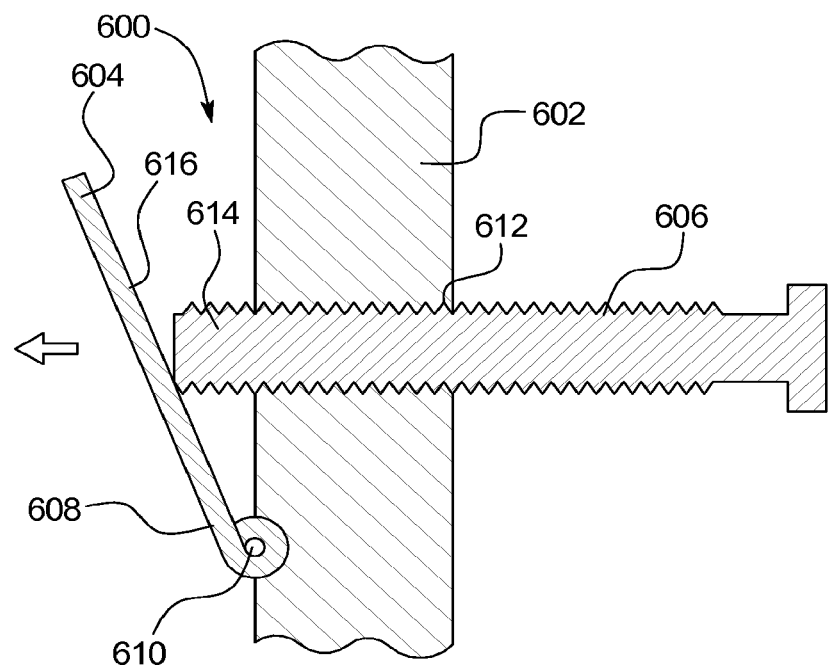
FIG. 10B is a cross-sectional view of the buttress element and intramedullary nail with the buttress element of FIG. 10A shown in a deployed position.

FIGS. 10A and 10B illustrate another embodiment of a buttress element 600 (as shown in FIG. 10B) and a section of an intramedullary nail 602. In this embodiment, the buttress element 600 includes a reinforcement member 604 and a support member 606. The reinforcement member 604 is a plate-like element that is pivotally connected to the intramedullary nail 602. In the illustrated embodiment, the bottom portion 608 of the reinforcement member 604 is connected to the intramedullary nail 602 by hinge 610. FIG. 10A shows the reinforcement member 604 in an initial or pre-deployed configuration, and FIG. 10B shows the reinforcement member 604 in a deployed configuration.

The reinforcement member 604 is in the initial or pre-deployed configuration when the intramedullary nail 602 is inserted into the medullary canal of the femur. Once the intramedullary nail 602 is the desired configuration, the support member 606, which includes threads, is inserted through the cortical bone and into threaded bore 612 passing through intramedullary nail 602. The support member 606 is rotated to advance the support member through the bore 612. As the support member is advanced, the distal end portion 614 of the support member 606 contacts the back surface 616 of the reinforcement member 604 and causes the reinforcement member 604 to pivot about hinge 610 to move the reinforcement member 604 into the deployed position. In the deployed position, the reinforcement member 604 contacts the cortical bone 106 in the lesser trochanter region to reinforce the bone in this area.

Figure 11A:
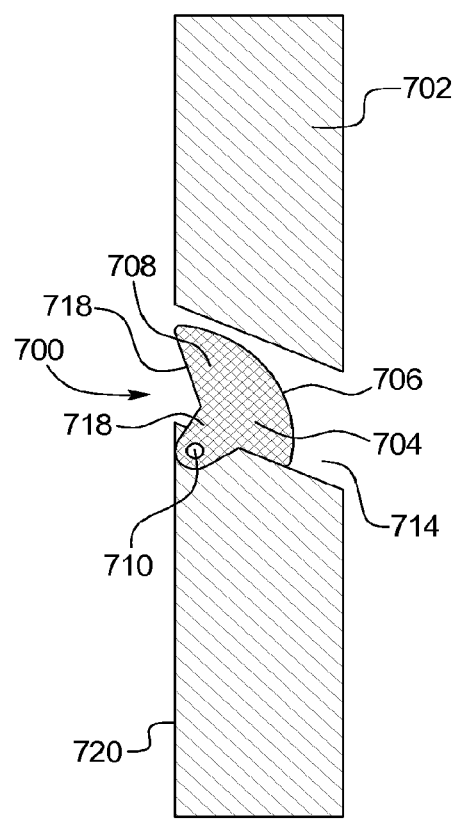
FIG. 11A is a cross-sectional view of another embodiment of a buttress element and a section of an intramedullary nail of the present disclosure shown in a pre-deployed position.
Figure 11B:
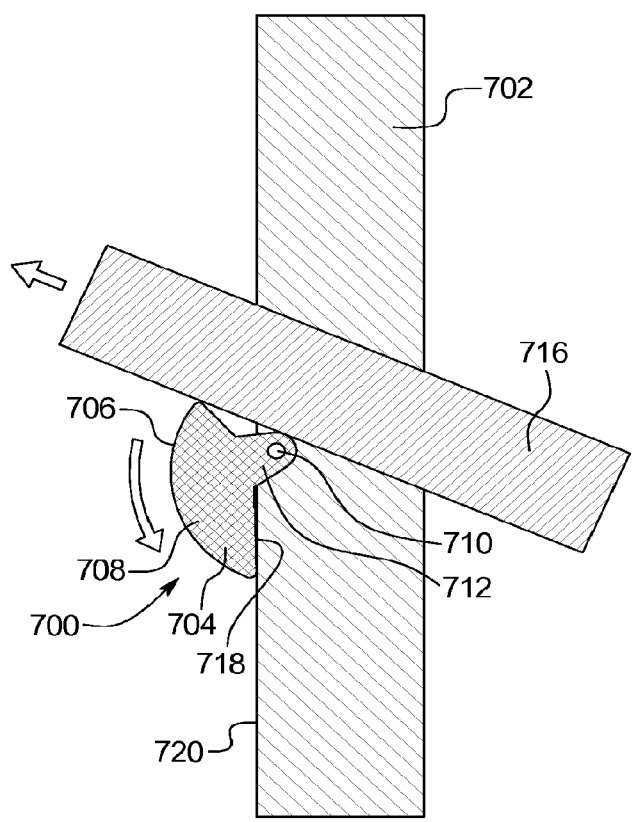
FIG. 11B is a cross-sectional view of the buttress element and intramedullary nail with the buttress element of FIG. 11A shown in a deployed position.

FIGS. 11A and 11B illustrate another embodiment of a buttress element 700 and a section of an intramedullary nail 702. The buttress element 700 includes a reinforcement member 704 that is pivotally or rotatably attached to intramedullary nail 702. In this embodiment, the reinforcement member 704 has a generally arcuate surface 706 and a generally hemispherically shaped body 708. In other embodiments, the reinforcement member 704 may have any other suitable shape and surface 706 may have any other suitable contour. Reinforcement member 704 may optionally includes one or more support members 712 that extend from body 708. Support member 712 is connected to the intramedullary nail 702 by hinge 710. FIG. 11A shows the reinforcement member 704 in an initial or pre-deployed configuration, and FIG. 11B shows the reinforcement member 704 in a deployed configuration.

In the pre-deployed configuration, reinforcement member 704 resides or is positioned in a passageway, channel, or cavity 714 defined by intramedullary nail 702. In one embodiment, reinforcement member 704 may be biased toward this position by a biasing mechanism, such as a spring or leaf spring. In other embodiments, the reinforcement member 704 may be held in the pre-deployed configuration by a releasable restraint or adhesive. In use, the intramedullary nail 702 is inserted into the medullary canal with the reinforcement member 704 in the initial or pre-deployed configuration shown in FIG. 11A. Once the intramedullary nail 702 is the desired configuration, an actuation member, such as an elongated member 716, which may be a screw, rod or the like, is inserted into, and optionally through, passageway 714 of intramedullary nail 702 as shown in FIG. 11B. Elongated member 716 contacts reinforcement element 704 and pushes or advances it out of passageway 714. In embodiments wherein reinforcement element 704 is biased toward the pre-deployed configuration, the force applied to reinforcement member 704 by elongated member 716 is sufficient to overcome the biasing force to move reinforcement element 704. In the embodiments wherein reinforcement member 704 is releasable restrained into the pre-deployed configuration, the force applied by elongated member 716 is sufficient overcome the restraint.

As reinforcement member 704 is moved out of the passageway 716, it rotates or pivots about hinge 710 into the deployed position. In the illustrated embodiment, bottom surface 718 of reinforcement member 704 contacts the outer surface 720 of intramedullary nail 702 when in the deployed position. In the deployed position, the reinforcement member 704 contacts the cortical bone 106 (shown in FIG. 4) in the lesser trochanter region to reinforce or buttress the bone in this area.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A femur fixation device for treating a femur, the femur having an intramedullary canal, a head portion and a lesser trochanter region, the fixation device comprising:
a one-piece elongated nail defining a longitudinal axis with a length along the longitudinal axis, a width perpendicular to the longitudinal axis that extends from a first side of the one-piece elongated nail to a second side of the one-piece elongated nail, and a bore extending through the one-piece elongated nail from the first side to the second side, the one-piece elongated nail configured for insertion into the intramedullary canal of the femur; and
a buttress element configured to extend from the one-piece elongated nail and apply a force to bone tissue in or adjacent to the lesser trochanter region of the femur, the buttress element including:
a support member having a distal end; and
a reinforcement member, the reinforcement member directly pivotally coupled to the one-piece elongated nail, wherein, at a first position, the reinforcement member is located adjacent to the one-piece elongated nail and is configured to engage with the distal end of the support member such that upon advancement of the support member through the bore, the reinforcement member pivots from the first position to a second position, and wherein, at the second position, the support member extends through the bore with the distal end contacting a surface of the reinforcement member such that a portion of the reinforcement member extends from the one-piece elongated nail.

2. The femur fixation device of claim 1, wherein the reinforcement member includes a plate-like member having a top portion and a bottom portion.

3. The femur fixation device of claim 2, wherein the bottom portion is directly pivotally coupled to the one-piece elongated nail and the top portion is the portion that extends from the one-piece elongated nail at the second position.

4. The femur fixation device of claim 2, wherein the top portion is directly pivotally coupled to the one-piece elongated nail and the bottom portion is the portion that extends from the one-piece elongated nail at the second position.

5. The femur fixation device of claim 1, wherein the reinforcement member is directly pivotally coupled to the one-piece elongated nail via a hinge.

6. The femur fixation device of claim 1, wherein, at the first position, the reinforcement member is at a first angle relative to the longitudinal axis, and wherein, at the second position, the reinforcement member is at a second angle relative to the longitudinal axis, the second angle greater than the first angle.

7. The femur fixation device of claim 1, wherein the bore is a threaded bore.

8. The femur fixation device of claim 1, wherein the support member includes an elongated rod.

9. The femur fixation device of claim 1, wherein the support member includes an elongated rod that is configured to engage with threads of the bore.

10. The femur fixation device of claim 1, wherein, at the second position, the support member extends radially from the one-piece elongated nail.

11. The femur fixation device of claim 1, wherein the reinforcement member and the support member are separate elements that engage each other, at the second position, to form the buttress element.

12. A femur fixation device for treating a femur, the femur having an intramedullary canal, a head portion and a lesser trochanter region, the fixation device comprising:
a one-piece elongated nail defining a longitudinal axis with a length along the longitudinal axis, a width perpendicular to the longitudinal axis that extends from a first side of the one-piece elongated nail to a second side of the one-piece elongated nail, and a bore extending through the one-piece elongated nail from the first side to the second side, the one-piece elongated nail configured for insertion into the intramedullary canal of the femur; and
a buttress element configured to extend from the one-piece elongated nail and apply a force to bone tissue in or adjacent to the lesser trochanter region of the femur, the buttress element including:
a support member having a distal end and configured to extend through the bore; and
a reinforcement member having a first surface and a second surface opposite the first surface, a portion of the reinforcement member directly coupled to the one-piece elongated nail at a coupling location, wherein the first surface is configured to engage with the distal end of the support member, and upon engaging with the distal end, the reinforcement member rotates about the coupling location.

13. The femur fixation device of claim 12, wherein the reinforcement member includes a plate-like member.

14. The femur fixation device of claim 12, wherein the support member extends radially from the one-piece elongated nail and the reinforcement member is located at the distal end of the support member.

15. The femur fixation device of claim 12, wherein, at a first position, the reinforcement member is at a first angle relative to the longitudinal axis, and wherein, at a second position, the reinforcement member is at a second angle relative to the longitudinal axis, the second angle greater than the first angle.

16. The femur fixation device of claim 12, wherein the support member includes an elongated rod.

17. The femur fixation device of claim 12, wherein the support member includes a threaded elongated rod that is configured to engage with threads of the bore.

18. A method of treating a femur, comprising:
  inserting a one-piece elongated nail into an intramedullary canal of the femur, the one-piece elongated nail defining a longitudinal axis, a length along the longitudinal axis, a width perpendicular to the longitudinal axis that extends from a first side of the one-piece elongated nail to a second side of the one-piece elongated nail, and a bore extending through the one-piece elongated nail width from the first side to the second side, wherein a reinforcement member is directly coupled to the one-piece elongated nail at a coupling location;
  inserting a support member through the bore such that a distal end of the support member contacts a surface of the reinforcement member; and
  advancing the support member such that the reinforcement member rotates about the coupling location and reinforces a lesser trochanter region of the femur.

19. The method of claim 18, wherein reinforcement member includes a plate-like member and the support member includes an elongated rod.

20. The method of claim 18, wherein the support member includes threads, and wherein advancing the support member includes rotating the support member such that the threads of the bore engage with threads of the bore.

* * * * *

UNITED STATES PATENT AND TRADEMARK OFFICE
CERTIFICATE OF CORRECTION

PATENT NO.        : 9,232,970 B2             Page 1 of 1
APPLICATION NO.   : 14/157556
DATED             : January 12, 2016
INVENTOR(S)       : Kyu Hyun Yang It is certified that error appears in the above-identified patent and that said Letters Patent is hereby corrected as shown below:

In the claims,

In column 12, line 5, in Claim 18, before "from", delete "width", therefor

Signed and Sealed this
Twenty-sixth Day of April, 2016

Michelle K. Lee
*Director of the United States Patent and Trademark Office*